United States Patent
Brocke

(10) Patent No.: US 8,554,324 B2
(45) Date of Patent: Oct. 8, 2013

(54) MOBILE DEVICE FOR TRANSCRANIAL AUTO-STIMULATION AND METHOD FOR CONTROLLING AND REGULATING THE DEVICE

(76) Inventor: Burkhard Brocke, Berlin (DE)

( * ) Notice: Subject to any disclaimer, the term of this patent is extended or adjusted under 35 U.S.C. 154(b) by 0 days.

(21) Appl. No.: 13/130,624

(22) PCT Filed: Nov. 20, 2009

(86) PCT No.: PCT/EP2009/065588
§ 371 (c)(1),
(2), (4) Date: Aug. 16, 2011

(87) PCT Pub. No.: WO2010/057998
PCT Pub. Date: May 27, 2010

(65) Prior Publication Data
US 2011/0288610 A1 Nov. 24, 2011

(30) Foreign Application Priority Data
Nov. 21, 2008 (DE) .......................... 10 2008 043 973

(51) Int. Cl.
*A61N 1/00* (2006.01)
(52) U.S. Cl.
USPC .......................................................... 607/45
(58) Field of Classification Search
USPC ..................................... 607/45, 46
See application file for complete search history.

(56) References Cited

U.S. PATENT DOCUMENTS

| | | | |
|---|---|---|---|
| 5,496,258 A | 3/1996 | Anninos et al. | |
| 6,445,955 B1 * | 9/2002 | Michelson et al. | 607/46 |
| 7,003,353 B1 * | 2/2006 | Parkhouse | 607/45 |
| 2006/0161218 A1 * | 7/2006 | Danilov | 607/45 |
| 2006/0173510 A1 * | 8/2006 | Besio et al. | 607/45 |
| 2007/0150025 A1 * | 6/2007 | Dilorenzo et al. | 607/45 |
| 2009/0082831 A1 * | 3/2009 | Paul et al. | 607/59 |
| 2010/0324441 A1 | 12/2010 | Hargrove et al. | |
| 2011/0004269 A1 | 1/2011 | Strother et al. | |

FOREIGN PATENT DOCUMENTS

| | | |
|---|---|---|
| DE | 10242542 A1 | 4/2004 |
| DE | 2020066020051 U1 | 12/2007 |
| DE | 102006053427 A1 | 5/2008 |

(Continued)

OTHER PUBLICATIONS

Fiedler et al., Neuromodulation durch Vagusnervstimulation bei Depression [Neuromodulation as result of vagus nerve stimulation in the case of depression], Journal fuer Neurologie, Neurochirurgie und Psychiatrie [Journal for neurology, neurosurgery and psychiatry], 2007, 8(4), 22-28—English abstract on p. 22.

*Primary Examiner* — Christopher D Koharski
*Assistant Examiner* — Michael Carey
(74) *Attorney, Agent, or Firm* — Laurence A. Greenberg; Werner H. Stemer; Ralph E. Locher

(57) ABSTRACT

A mobile device for transcranial auto-stimulation and a method for controlling and regulating the mobile device are provided. The mobile device is controlled according to need, of circumscribed brain structures and brain systems. The device for transcranial electric current stimulation includes the following components:—electrodes with fasteners to exactly position the electrodes on the skin of the head and electrical connecting lines and—a transportable, miniaturized stimulation generator comprising a current generator, a controller, a user interface, an electrical energy storage device and a monitoring and safety module with a separate electrical energy storage device.

14 Claims, 4 Drawing Sheets

(56) References Cited

FOREIGN PATENT DOCUMENTS

| | | | |
|---|---|---|---|
| EP | 0497933 | B1 | 3/1999 |
| WO | 2007079181 | A2 | 7/2007 |
| WO | WO 2007079181 | A2 * | 7/2007 |
| WO | 2007136726 | A2 | 11/2007 |
| WO | 2009039294 | A1 | 3/2009 |
| WO | 2009097526 | A2 | 8/2009 |
| WO | 2009137683 | A2 | 11/2009 |

* cited by examiner

MOBILE DEVICE FOR TRANSCRANIAL AUTO-STIMULATION AND METHOD FOR CONTROLLING AND REGULATING THE DEVICE

BACKGROUND OF THE INVENTION

Field of the Invention

The invention relates to a mobile device for demand-driven transcranial auto-stimulation of circumscribed brain structures and brain systems, and to a method for controlling and regulating the device.

A device for mobile, demand-driven auto-stimulation of circumscribed brain structures and brain systems should be understood to mean a device for transcranial electrostimulation (TES), which can be used for controlling behavior, independent of location, by any user in an autoregulatory fashion and which is used in a method for neurostimulation. The term auto-stimulation should be understood within the scope of a user of the device stimulating him/herself, as a result of which special features of the medical-technical device are derived, particularly in respect of safe handling of the device.

Circumscribed brain structures should be understood to mean brain structures that, in their totality, form a functional unit and control individual neurocognitive processes, for example processes of fear regulation. The circumscribed brain structure need not necessarily be circumscribed in a spatial sense, but can extend in a network-like fashion over a relatively large region, with deep and shallow brain areas being part of the network. It is predominantly shallow areas of the relevant network that can be considered for stimulation; these areas lie just below the skull cap and can be reached by transcranial stimulation. The transcranial neurostimulation of the brain influences brain structures and brain systems, and the neuronal processes carried out therein, in particular by targeted changing of neuronal membrane potentials and firing rates.

The influenced processes primarily are neurocognitive processes in behavior regulation, such as the neuroregulation of attentiveness, processes in fear regulation and neurocognitive processes of target-following and target-screening, wherein the screening or amplification of action intents takes place with respect to competing action intents. In very general terms, the neurocognitive processes in behavior regulation play a decisive role in a multiplicity of types of behavior, for example when adjusting attention performance to different requirements, when efficiently implementing action intents, efficiently regulating fear or regulating other emotional states, or in the case of various mental disorders, such as depressive disorders. Furthermore, efficient behavioral control in the case of substance abuse and dependence, or substance withdrawal, is also affected, for example in the case of tobacco products, alcohol, drugs, eating behavior or compulsive gambling and risk behavior.

Various concepts are known in the field of the neurostimulation of brain structures. These include deep electrical stimulation, transcranial magnetic stimulation (TMS) and transcranial electrical stimulation (TES), in particular transcranial direct current stimulation (tDCS) and transcranial random noise stimulation (tRNS). In particular, the following methods and devices are known, wherein a distinction can be made between invasive and non-invasive methods.

In the case of invasive methods, a stimulator for neurostimulation of the outer spinal meninges in the case of angina pectoris has been disclosed, wherein the stimulator is implemented operatively.

Furthermore, the prior art has disclosed a stimulator for one of the twelve cranial nerves, the vagus nerve, which stimulator is used in the case of severe depression and is likewise implemented operatively (Fiedler, U. & BajBouj, M., 2007, Neuromodulation durch Vagusnervstimulation bei Depression [Neuromodulation as a result of vagus nerve stimulation in the case of depression], Journal für Neurologie, Neurochirurgie and Psychiatrie [Journal for neurology, neurosurgery and psychiatry], 8(4), 22-28).

Furthermore, deep electrodes have been disclosed, which are inserted into deep areas of the brain by surgery in the case of severe, therapy-resistant depression.

It is primarily transcranial magnetic and electrical brain stimulation methods that are known as methods for non-invasive neurostimulation of the brain. In the case of transcranial magnetic stimulation (TMS), a magnetic coil over the surface of the head is used to apply a very brief magnetic field with a duration of less than one millisecond (ms). The magnetic field has an intensity of approximately one to two teslas. The magnetic field passes through the skull and induces a very brief current flow. This in turn produces neuronal discharges in a tightly delimited area of a few cubic centimeters. Thus, the coil current is first of all translated into magnetic energy and then converted into current in the neurons. Repetitive TMS (rTMS) is known in addition to this above-described single-pulse TMS. In rTMS, a large number of pulses are applied in a prescribed sequence. High pulse rates increase the cortical excitability while low pulse rates of e.g. 1 hertz inhibit the cortical excitability.

In the case of transcranial direct current stimulation (tDCS), a weak continuous direct current is applied via two large-area electrodes on the scalp. This brings about a small shift in the membrane potential of cortical neurons and a change in the firing rate, and hence the excitability level thereof is influenced; to be precise, it is increased or reduced, depending on the polarity of the stimulation. In the case of anodal stimulation (the positive pole is in the vicinity of the cell body or the dendrites), depolarization is brought about by increased membrane potentials and firing rates, and hence increases the excitability. In the case of cathodal stimulation, the neurons are hyperpolarized as a result of lowered membrane potentials and firing rates, and the excitability is reduced.

In the case of transcranial random noise stimulation (tRNS), an oscillation spectrum is applied for a signal with, for example, a 1 mA current and randomly distributed frequencies between—this depends on the sampling rate—0.1 and 640 Hz, for example. In the process, all coefficients in the frequency spectrum have the same magnitude ("white noise"). This achieves an effect that is comparable to anodal tDCS: an increase in the excitability of circumscribed areas of the brain. Advantages include a greater independence of the direction of the current flow from the cortex gyri. Since no polarization is created as a result of the oscillation, this moreover renders it almost impossible for the current flow to be hardly noticed by the user on occasion.

The so-called long-lasting excitability changes are of particular interest for practical applications. In the case of repetitive transcranial magnetic stimulation (rTMS) and transcranial electrical stimulation (tDCS, tRNS), the excitability changes are proportional to the number of repetitive TMS stimuli or to the duration of the electrical stimulation. However, they are maintained for a limited period of time following the stimulation duration as a result of an after effect or long-term effect. In the case of applications that are connected to changes in the neuronal excitability, for example in the case of neurological dysfunctions, this results in influencing over slightly longer periods of time. In the case of an anodal direct current stimulation of approximately 15 minutes, this makes excitability increases of up to two hours possible; a 10 minute cathodal direct current stimulation can induce long-term effects of up to one hour.

The length of these after effects depends on the induced overall charge in the case of tDCS and on the number of repetitive pulses in the case of rTMS. The induced overall charge in tDCS emerges from the current, the electrode area, and the stimulation duration when combined according to the following formula:

Induced overall charge=current/electrode area×stimulation duration.

In the case of direct current stimulation, a maximum interruption-free stimulation duration of 15 minutes may be attained; however, this stimulation duration should not be exceeded at present for reasons of safety. As a result, the maximum action duration achievable at present without pulse repetition in the case of cathodal induction is approximately one hour and it is approximately two hours in the case of anodal induction; this significantly limits the use.

A device for transcranial influencing of the central nervous system in the case of dysfunctions is described in EP 0497933 B1. In particular, a magnetic field is used therein for compensating epileptic foci for treating epilepsy. Use is made of low frequency (2 to 7 hertz), low strength (0.5 to 7.5 picotesla) magnetic fields. An arrangement of a plurality of electromagnets in a special headgear allows the locally assigned application of the magnetic fields, as required. A generator controls and emits the energy required for operating the electromagnets.

The further, known non-invasive stimulators as per the prior art are additionally disadvantageous in that someone who is not a pre-trained medical practitioner skilled in the art is unable to apply them because the respectively suitable stimulation parameters have to be set manually by a medical practitioner skilled in the art in equipment provided for the therapy. Moreover, in the case of invasive stimulation methods, the considerable burdens and possible risks associated with the surgical intervention are a significant disadvantage.

A device for transcranial neurostimulation by means of a special electrode arrangement is disclosed in US 2006/0173510 A1.

A decisive disadvantage of the non-invasive equipment and methods is the requirement of stationary equipment as part of the device, and so the application is tied to a certain location. If there is an acute need for stimulation, this can only be fulfilled if the person to be stimulated is in the direct vicinity of the stimulator. If the person to be stimulated departs from the location, it is only possible to use an after effect, which, depending on the stimulation, is retained for no more than two hours. In the case of distance from the stimulator, the location of the equipment and the maximum obtainable effect duration (maximum after effect) thus also limit the use time and the movement range of the user. Repeated stimulation (with a pause for reasons of safety after 15 minutes) is not possible due to the distance from the equipment. Hence, the maximum effect duration that can be achieved at present is unsuitable for the envisaged purpose because it is necessary to cover all parts of the day when the user is awake.

According to U.S. Pat. No. 6,445,955 B1 and DE 10 2006 053 427 A1, the prior art discloses devices for transcutaneous muscle stimulation, which can be transported and used on the move. However, this equipment for transcutaneous neurostimulation is designed such that the stimulation of muscles is carried out as a measure in physiotherapy and sports medicine, and also for restoring muscles after operations or the like. From a technical and medical point of view, this equipment is unsuitable for transcranial neurostimulation, which, qualitatively, has significantly different requirements for suitable devices and the effects thereof on the human brain.

BRIEF SUMMARY OF THE INVENTION

The object of the present invention is to specify a device for transcranial auto-stimulation and a method for controlling and regulating the device, which are designed in a technical sense such that, unlike in transcutaneous electrostimulation, neuronal membrane potentials in prescribed target areas are influenced in an effective fashion and that, in addition to the highest levels of operational safety of the device, the mobility of the user of the device is also a given.

According to the concept, the object is achieved by a mobile device for transcranial auto-stimulation, which comprises the following components:

electrodes with attachment means for precise positioning on the scalp and electrical connection lines and a transportable, miniaturized stimulation generator with a current generator, a control unit, a user interface, an electric energy reservoir and a monitoring and safety module with a separate electric energy reservoir.

According to the concept, the control unit of the stimulation generator contains at least one program for determining the pulses to be emitted by the current generator in respect of the value range of the electrical, topographic and temporal parameters for the intended change of the neuronal membrane potentials in the target area, which value range is permissible and necessary for the target area and for the intended use. In particular, five parameters are used for this purpose: the current, the stimulation duration, the electrode area, and the electrode position and, optionally, the electrode polarity—anodal or cathodal—for aligning the electric field. The overall amount of charge and the current density are derived from these variables. Depending on intended use, different programs are saved on the control unit such that they can be called, which programs are used, for example, in the case of different clinical pictures and for this purpose have to reach different target sites in an effective fashion via the precise determination of the parameter values.

A user interface of the stimulation generator has program selection buttons that are used to select the program for the respective clinical picture.

It is important in the case where the mobile device is used by medical laymen that they can select stimulation protocols from within the programs, independently and according to their needs. To this end, function call buttons are provided in the user interface.

The user interface is completed by a display.

The monitoring and safety module is of great importance in the overall concept of the device; said module monitors, controls and regulates the correct mode of operation of the device. The monitoring and safety module is equipped with a separate electric energy reservoir in order to ensure the highest possible level of monitoring security.

A particular advantage of the device according to the invention consists of the fact that it can be applied by the user him/herself as an auto-stimulation for demand-driven auto-stimulation without dispensing with essential functions of transcranial stimulation; this can be done in an uncomplicated and operationally reliable fashion, independently of location and whilst on the move in the most diverse application situations. According to the concept, the device is designed and secured such that no medically pre-trained staff is required for routine use. This is a substantial advantage compared to other devices known from the prior art.

The microcontroller of the monitoring and safety module is equipped with a simple yet efficient, extremely energy-saving current supply, which has an operational-current-independent battery backed-up current supply in the case of a malfunction. The monitoring apparatus safeguards against malfunctions in the program flow or deviations in the stimulation procedure from the control algorithm, and against a crash of the control software. To this end, the monitoring and safety module is equipped with a watchdog system, which demands a precisely set signal sequence from the program after respectively one unit of time, for example every 10 ms. Should the signal sequence fail, the monitoring apparatus generates a reset of the control and, if necessary, forces a restart of the software.

A preferred embodiment of the invention consists in the application for transcranial direct current stimulation. Here the current generator is embodied as a direct-current generator and two electrodes are provided on the scalp.

The neuronal discharge rates, and hence the activity and excitability in the target area, are increased in the case of anodal alignment of the current-flow direction and inhibited in the case of cathodal alignment of the current-flow direction.

An advantageous embodiment of the invention consists of the fact that the function call buttons for calling a stimulation protocol from a program by the user, or the entire user interface, are designed as a remote control for the stimulation generator. As a result, the user of the device can thereby carry out the direct operational functionality via the function call buttons in an uncomplicated fashion. In this case, the remote control has a wireless or wired embodiment, the wireless embodiment allowing a particularly inconspicuous application of the device in everyday situations. Advantageously, smartphones, cellular telephones or PDAs can also be used as a remote control, on which buttons are assigned as function call buttons, with the instruments having corresponding interfaces on which tailored programs can run.

The monitoring and safety module preferably has a separate microcontroller and uses a capacitor as a separate energy reservoir for a battery backed-up current supply in the case of a malfunction.

The electrodes generally respectively have an area of between 25 and 35 cm$^2$.

According to a particularly advantageous development of the invention, the electrodes are formed from electrode partial areas with an area of less than 25 cm$^2$. Here, a multiplicity of electrode partial areas are arranged in a grid-like fashion, wherein the areas acting as electrodes are formed by actuating one or more electrode partial areas.

This embodiment is particularly advantageously developed by the electrode partial areas being integrated into a headgear because various application options are connected with a universal headgear containing a multiplicity of electrode subregions, without the device, and the medical application connected therewith, being visible to outsiders.

The stimulation generator is connected to the multiplicity of electrode partial areas, which are positioned in a grid-like fashion and situated in the headgear, via connection lines. In this case, the control unit is designed such that, in accordance with the program to be carried out, it only actuates the electrode partial areas for the region to be stimulated.

A headgear should, in the broadest sense, be understood to mean embodiments that allow a locally precise positioning of the electrodes, which are integrated into the headgear. Here, band constructs, hats, caps, and helmets should be mentioned in an exemplary fashion.

A further advantageous embodiment consists of the stimulation generator alternatively being integrated into the headgear, or being integrated therein together with the electrodes or electrode partial areas. In this case, the headgear is expediently designed in a helmet-like fashion in order to ensure sufficient stability. In this embodiment of the invention, the user interface is advantageously arranged in a separate remote control, which is connected wirelessly, in order to be able to operate the stimulation generator without having to remove the headgear.

In addition to the technical preconditions for transcranial electrostimulation, it is an advantageous addition for the device for transcranial electrostimulation to contain a speech module with headphones or loudspeakers, which speech module is preferably integrated into the stimulation generator, or else designed to be separate from the stimulation generator, and in any case is coupled to the stimulation protocol. Audio sequences, matched to the current electrical stimulation parameters, are saved in the stimulation protocol and support the application and effect of the stimulation.

This allows a combination of spoken instructions, from therapy and behavior programs, and transcranial stimulation; this allows a particularly effective use of the device.

An advantageous development of the invention consists of the stimulation generator having an attachment band for attaching it to the body of the user, for example to the upper arm, the hand or the wrist, or to the chest of the user. Together with the wireless remote control with the function call buttons, the user interface is designed to act on the control unit and, together with the stimulation generator, connected to the electrodes via the connection lines.

According to an advantageous embodiment of the invention, the stimulation generator is designed with an attachment band, which is embodied as an armband, for attaching it to the wrist of the user, wherein the user interface is integrated into the stimulation generator and the latter is connected to the electrodes via the connection lines. Alternatively, a wireless remote control is advantageously provided for the control unit of the stimulation generator, which remote control at least has function call buttons.

For the purpose of controlling and regulating the device, electrodes or electrode partial areas are advantageously designed as sensors for establishing the contact resistance, wherein the signals from these sensors are processed by the monitoring and safety module.

As a result, the optimum electrode area required for a treatment may be calculated and switched by the control unit, depending on the selected program. Hence, erroneous operations are excluded in respect of the electrode size as a function of the type of treatment. Furthermore, the required strength of the stimulation current over the permissible minimum total electrode area is obtained by calculating the required optimal electrode area, taking into account the contact resistance in the interest of precise focusing of the induced overall charge in the target area.

A substantial and surprising discovery that led to the present invention is that the medical consequences of the transcranial stimulation are reflected in the technical implementation of the monitoring and safeguarding of the electrical parameters of the stimulation. Since a transcranial autostimulation is carried out directly in the brain of the human, precise controlling and monitoring of the stimulation and the parameters used is of the utmost importance.

This discovery has three aspects. First of all, the device had to be designed such that (1) the required influencing of the membrane potentials is achieved; that (2) the user him/herself can use the device without danger; and that (3) the device has a high degree of safety in terms of its functionality.

The first and the second aspect are predominantly satisfied by the technical embodiment of the device with the control module, and the program selection and function call buttons.

The third aspect—the monitoring and safeguarding during use—is implemented by a method for controlling and regulating the device, by means of which method the duration and strength of the stimulation is monitored in respect of the respectively permissible variable. The stimulation procedure, and all involved components, e.g. the electrode resistances, are monitored and the system is reset if need be.

The method contains the following steps:
a) selecting a program by means of the program selection button on the user interface,
b) using the function call buttons to select and call a stimulation protocol for a stimulation unit, which, in the target area of the cortex fixed for the application, brings about the change in the neuronal membrane potential and the firing rate in terms of the desired and possible strength for the desired and permissible duration,
c) monitoring and limiting the stimulation by means of the monitoring and safety module of the stimulation generator.

In this system, the parameters current, voltage, stimulation duration, electrode position, and electrode area are the directly measureable and influenceable parameters, which are matched to one another such that the overall amount of charge and the maximum current density are not exceeded.

By way of example, an electrode detachment can be detected during monitoring in the case of a gradual increase in the electrode resistance over a period of minutes or seconds. In this case, the stimulation current must be reduced proportionately in order to keep the current density constant and to exclude tissue damage as a result of an excessive current density. The system is shut down if prescribed limit values are exceeded.

A pulsed change in the electrode resistance allows the conclusion to be drawn that there is a line break or a loose contact. This also requires attention to be drawn thereto. The stimulation current is markedly reduced or switched off in the case of a brief break because the thresholds for damage, pain and irritation are much lower in the case of pulsed stimulation than in the case of a direct current.

The overall amount of charge used for the stimulation is a further derived parameter. It is necessary to establish the induced overall amount of charge permanently in order to calculate the still remaining stimulation duration of a particular stimulation operation and to exclude overshoots.

In a further embodiment of the method according to the invention, the electrodes, which are positioned in a grid-like fashion in the helmet and designed as sensors, measure the contact resistance; the measured value is reported to the control unit and processed. For the purposes of the stimulation, an appropriate number of the multiplicity of electrodes, positioned in a grid-like fashion, are actuated in order to obtain the required strength of the stimulation current.

In summary, the medical concept as the background to the present invention can be described as follows:

The device according to the invention can be used to generate stimulation protocols, which are mainly characterized by the following parameters: pulse duration, pulse strength, electrode area, and amount of charge, and also by the electrode positions and electrode polarities for aligning the electric field. As a result, certain brain areas and neuronal circuits are either activated or deactivated in an effective fashion, or are inhibited, depending on the object of the application and the neuronal processes on which this is based.

By way of example, this relates to the dorsolateral prefrontal cortex (DLPC), the ventromedial prefrontal cortex (vmPC), the temporal cortex (TK), or the insula.

Substantial advantages and hence associated features are:
a miniaturized design as a result of an extremely current-saving watchdog system as part of the monitoring and safety system, which has an operational-current-independent battery backed-up current supply in the case of a malfunction, a separate operating unit and a special controller;
application advantages thereof are given by location independence (mobility), mobile usage not restricted by time and space, and by being able to be worn on the body in a covered fashion,
function call buttons for simple and reliable calling of electrical pulses with different characteristics while the program is running, simple operability as a result of a plurality of buttons, which are systematically matched to one another;
application advantages thereof are given by the option of auto-stimulation by a simple and safe application by the user,
stimulation protocols, which are individual and demand-driven, and in which the parameters of the respectively suitable stimulation are fixed in a precise fashion; application advantages thereof are given by the option of a safe, individual, and demand-driven auto-stimulation by the user,
separate function call buttons as central functional units of the user interface or a remote control;
application advantages thereof are given by a use that is completely independent of the situation, for example at work; the stimulation generator can be worn covered up in the headgear or on the body,
the ability to actuate the electrode pattern or electrode array in a variable fashion and there being automatic impedance monitoring;
application advantages thereof are given by an individually adapted selection of the electrode position, and increased effectiveness and flexible actuation depending on the preselected program,
a miniature stimulation generator and electrode array that is integrated into the headgear as a functional unit.

The medical application of the device is brought about as follows, illustrated in an exemplary fashion for a transcranial direct current stimulation:

The large-area electrodes, which have to be positioned in a precise fashion to ensure that the target area is reached, make contact with the scalp. A static electric field is generated by means of a weak, continuous current flow—a direct current pulse; said electric field is used to modulate the neuron activity in the brain or in the target area. The neurons respond to the electric field with a small shift in the membrane potential and with a modified firing rate, which changes their excitability. The rest potential, the firing rate and the excitability are increased in the case of anodal stimulation, and they are decreased in the case of cathodal stimulation.

These inhibiting or exciting membrane potential shifts or changes in the excitability are used for targeted influencing of circumscribed, i.e. spatially or functionally limited, neuronal circuits and areas, which are the basis for the behavior relevant in this case, for example attentiveness regulation, target-following and target-screening, fear regulation, substance abuse and substance withdrawal, or eating behavior.

Functional activation or inhibition processes of these circuits are induced or amplified, dysfunctional activation or inhibition processes are inhibited or blocked.

The neuronal circuits on which the processes of behavior regulation are based can be effectively influenced in the areas situated close to the surface of the cortex. By way of example, the following is suggested at present for the behavior regulation processes listed in an exemplary fashion:

Substance Abuse:
Controlling alcohol consumption: anodal stimulation of the DLPC,
Nicotine: anodal stimulation of the DLPC, cathodal stimulation of the insula (inferior PFC/temporal cortex),
Controlling Eating Behavior:
Bulimia: cathodal stimulation of the insula,
Anorexia nervosa: anodal stimulation of the insula,
Neuroregulation of the attentiveness: anodal stimulation of the DLPC,
Attentiveness and working memory: anodal stimulation of the inferior frontal gyrus (IFG).

The advantages in applying the device according to the invention consist of improving neurocognitive processes in behavior regulation, implementing efficient behavior control, for example efficient behavior control in the case of substance abuse or substance withdrawal (smoking, alcohol, drugs) and in the case of eating behavior, and in controlling and containing fear states (efficient fear regulation), and, furthermore, in neuroregulating the attentiveness.

What should be highlighted in particular is that:
neuronal processes can be selectively activated or inhibited,
it is possible to repeat the stimulation without limitations below the limit values for the induced overall amount of charge,
it is possible to use it on the move without limitations and independently of time and location as a result of the miniaturized design and operational-current-independent monitoring and safety system,
it is possible to use it independently of the situation even during everyday life as a result of separate function call buttons with a radio connection,
strictly demand-driven auto-stimulation is possible
(flexible selection of specialized treatment programs, such as neuroregulation of the attentiveness, neurocognitive processes of target-following and target-screening, processes in fear regulation, behavioral control in the case of substance dependence or eating disorders, the ability to recall individual tailored stimulation protocols, flexible individual selection of electrode positions), and
there can be a lower dosage compared to when using the after effect, for example, as a result of the stimulation being able to be repeated any number of times.

Further details, features and advantages of the invention emerge from the following description of exemplary embodiments, with reference being made to the associated drawings. In the figures:

DESCRIPTION OF THE INVENTION

Figure 1:
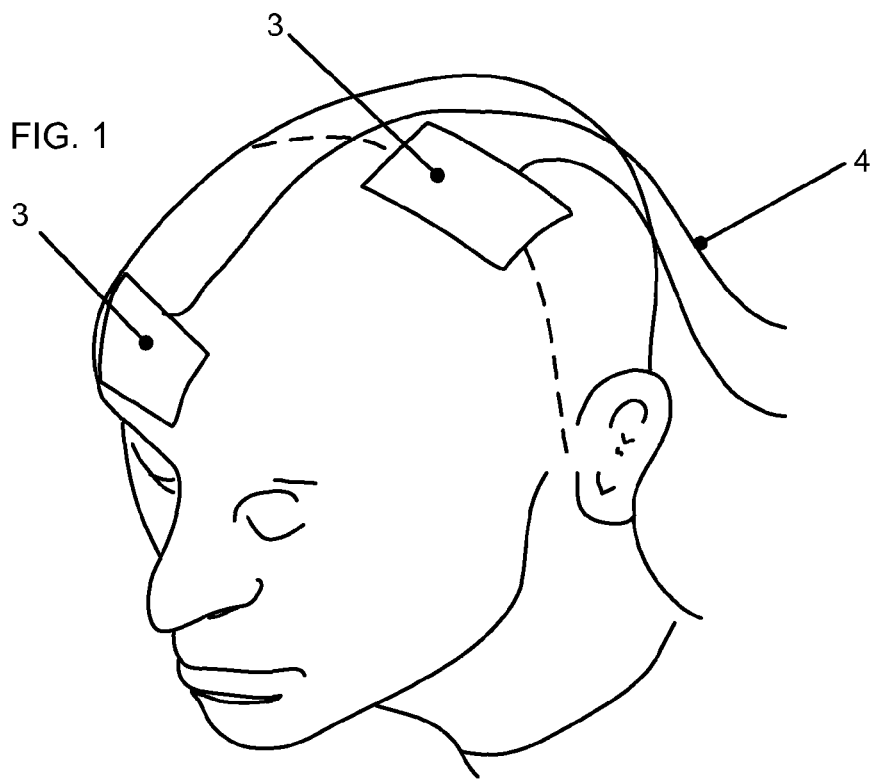
FIG. 1 shows an electrode arrangement in the case of transcranial direct current stimulation.

FIG. 1 shows the head of a user of a device for direct current stimulation with applied electrodes 3, which are switched as cathode and anode, and also the connection lines 4 required for routing direct current pulses from the direct-current generator (not illustrated) to the electrodes 3. The precise localization of the electrodes 3 is set in each case such that the electric field reaches the brain area suited to the respective application as precisely as possible. The precise positioning required for the respective application can, according to known methods, be brought about using a neuronavigator or with the aid of landmarks. Setting the target area is detailed in the operating instructions of the electrostimulation unit and is undertaken by the user. Matched to this are the stimulation protocols, which are provided for the respective application situation and represent the pulse characteristic, the current, and the stimulation duration, defined in the control program, which is stored in the control unit (not illustrated).

For safe operation, provision is made in an embodiment (not illustrated here) for a helmet as a headgear with electrodes 3 installed therein, which helmet is placed onto the head of the user. The helmet has a hat on the interior thereof, the latter fitting to the head of the user and being used to precisely position the electrodes 3. In an advantageous embodiment, the helmet has a number of electrode partial areas arranged in a grid. The electrodes 3 are installed in the helmet in fixed positions and connected to the direct-current generator such that the electrode partial areas are actuated by pulses—either individually or in groups. The control unit and the program saved therein determine how the interconnection works for stimulating the target region in the brain.

An advantageous embodiment moreover consists of the electrodes or the electrode partial areas being designed as sensors for establishing the contact resistance, with the parameters thereof being used by the control unit to calculate the optimization of the actuation of the electrode partial areas in the case of varying contact resistances.

The actively actuated electrodes are then supplied with electrical energy in accordance with the selected program and the called stimulation protocol, and transmit the impulses, which are formed by an electric current with a certain magnitude and fixed duration, to the relevant circumscribed brain regions via the scalp. The other, inactive electrodes in the electrode cap do not have a function in this phase and, where appropriate, are used when carrying out a different program or another stimulation protocol. The integration of the stimulation generator into the electrode cap such that there are short paths for the electrical connection lines is particularly advantageous. The stimulation generator is operated by means of a remote control, on which the user interface with the function call buttons is arranged.

Figure 2:
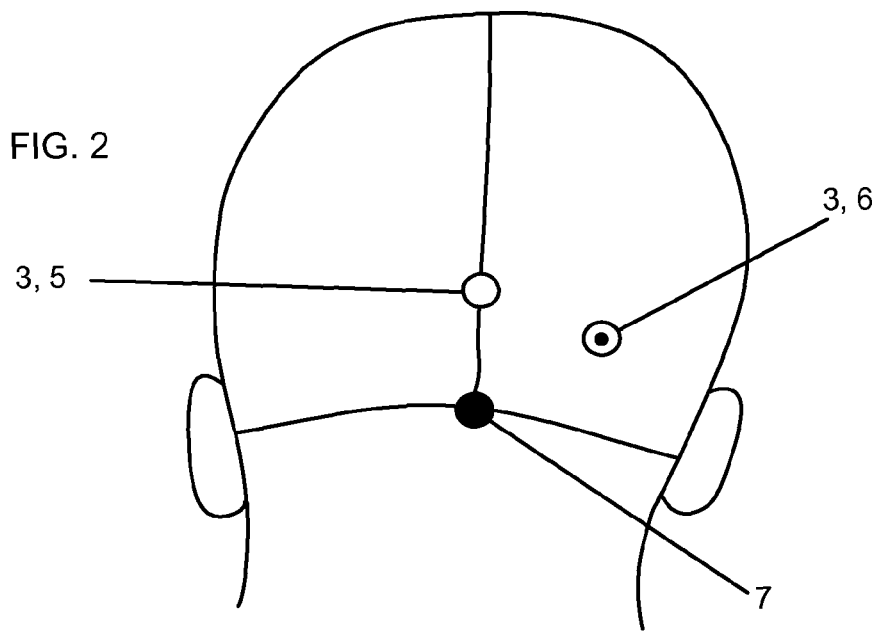
FIG. 2 shows the back of the head with the electrode positions.

FIG. 2 shows the back of the head of a user of the device with the arrangement of the electrodes 3 and demonstrates the use of so-called landmarks. By way of example, if landmarks are used, the line between the inion 7, the palpably soft point between the lower end of the skull and the upper end of the cervical spine, and the nasion, the transition between the dorsum of the nose and the forehead, is used as an initial point for establishing the position of the electrodes 3, which is fixed for the respective application.

In the illustrated example, the cathode is arranged 3.5 cm above the inion 7 and the anode 6 is 4.5 cm to the right of the cathode 5. A stimulation of the visual system is made possible in this exemplary embodiment.

The large-area electrodes 3, which have to be positioned in a precise fashion, make contact with the scalp in the illustrated embodiment. Then, a small membrane potential shift of cortical cells is induced in defined areas via a weak, continuous current flow in the form of a direct current pulse. Depending on the direction of the current flow, this shift in the membrane potential brings about an increase in the neuronal discharge rates in the case of an anodal alignment, or inhibits these in the case of a cathodal alignment. In addition to the current flow direction and the electrode position, these activation or deactivation processes depend on the exposure duration, the effective current density and the predominant position of the neurons with respect to the current-density vector. Hence the effect of this transcranial direct current stimulation (tDCS) can be dosed by the electrical parameters and can be localized by the electrode arrangement. The stimulation current is between approximately 0.001 and 0.002 ampere, and can be polarized in an anodal or cathodal fashion. However, depending on the other parameters, it may be increased to 0.005 ampere.

Figure 3:
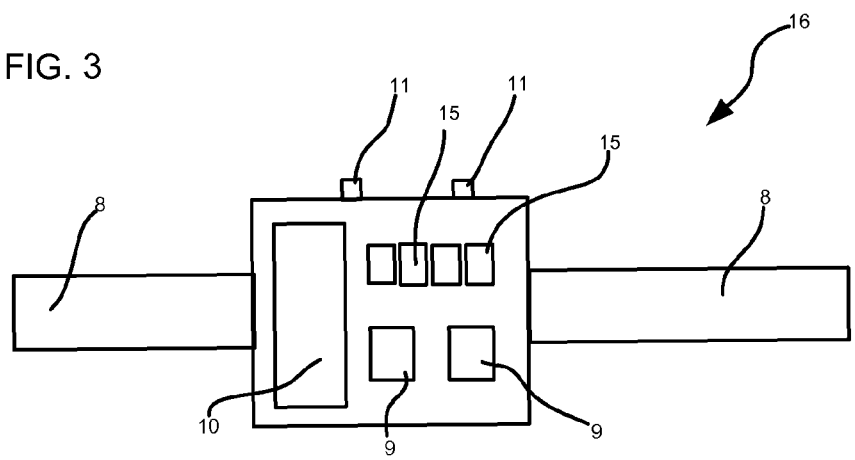
FIG. 3 shows a view of the electrostimulation unit with user interface, control unit and direct-current generator.

FIG. 3 shows an embodiment of the stimulation generator 16, which comprises the direct-current generator, the control unit and the user interface and on which provision is made for an attachment band 8. The attachment band 8 is designed as an armband for attaching the stimulation generator 16 to the forearm of the user or as a belt for fixing it to the body of the user. In the illustrated exemplary embodiment, the stimulation generator 16 furthermore has two connectors 11. The connection lines 4 (not illustrated here) to the electrodes 3 are attached thereto via suitable connection plugs, and the electrodes 3 are connected to the direct-current generator of the stimulation generator 16.

No remote control for external operation of the stimulation generator 16 is required because the user interface contains the function call buttons 15. Then, the function call buttons 15 can be operated on the same surface like the program selection buttons 9 of the user interface. In this embodiment variant, the stimulation protocols are called via the function call buttons 15 directly on the stimulation generator 16. In order to avoid operating errors by the user in e.g. stress situations, the program selection buttons additionally have a design that is secured by code.

The stimulation program is activated, or, should multiple programs be available, the desired program is selected, via the program selection buttons 9 of the user interface. The number of programs itself and the relevant specific parameters of the programs are prescribed and preset by the device manufacturer and are protected by a usual coding method to safeguard the intended use of the device against improper modifications.

An alternative embodiment (not illustrated) with high levels of operating comfort, which is predominantly suitable for undercover use in various everyday situations, consists of use being made of an external remote control with function call buttons for calling the stimulation protocols, which remote control is used to call the pulse characteristics according to the stimulation protocol, which pulse characteristics are suitable for the respective application situation and set in the program. For reasons of security and thwarting manipulation, the remote-control signal is encrypted such that influencing by another remote control or a similar signal is excluded.

The control unit of the device is integrated into the stimulation generator 16 and controls the stimulation and the current regulator, and guides the use protocol.

However, operation of the monitoring and safety module is particularly energy saving, independent and designed not to fall back on the energy resources of the stimulation generator in the case of a malfunction.

When operating the device via the external remote control or the user interface integrated into the stimulation generator, the user initiates a stimulation by pressing one of the function call buttons 15, wherein each of the function call buttons 15 allows a different amount of discrete induced overall charge within the scope of the value range prescribed by the set program, and allows this to be called.

Moreover, it is possible to call information from the remote control or the user interface and let it be displayed on the display 10. The display 10 displays information relating to the visual checking of the current operating action of the active stimulation program and, if applicable, further parameters such as the percentage of maximum amount of charge, duration of the treatment, duration of the pulses, type of pulses, charge-state display of the battery, and the like.

Figure 4:
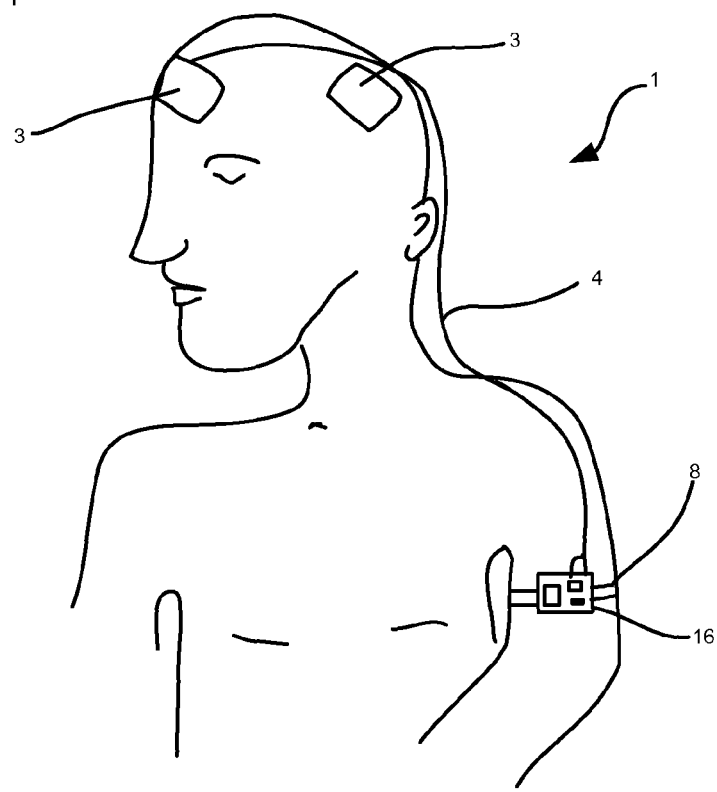
FIG. 4 shows an arrangement of the electrostimulation unit on the upper arm of the user.

FIG. 4 schematically shows a user with an applied neurostimulation device 1 for transcranial random noise stimulation (tRNS), with the stimulation generator 16 being applied to the upper arm. In this case, use is made of a remote control, by means of which the program can be started and the pulse duration and pulse strength can be selected via the function call buttons. For security reasons, the signal from the remote control has been encrypted by an encryption method known to a person skilled in the art such that influencing by another remote control or a similar received signal is excluded.

The attachment band 8, designed as an armband, is used to attach the stimulation generator 16 to the upper arm of the user. The electrodes 3 are situated on the head of the user in the position set for the purpose of the application. The current generator integrated into the stimulation generator 16 and the electrodes 3 are connected by means of the electrical connection lines 4, as a result of which the stimulation current from the current generator is routed to the electrodes 3.

Using the above-described tRNS renders it possible to increase the cortical excitability in the target area. This effect can be achieved particularly well at relatively high frequencies between e.g. 100 and 640 Hz, to be precise by repeated and rapid opening of cell sodium channels (Na+). In this case, the smaller stimulation electrode of e.g. 20 cm$^2$ is placed over the target area and the larger reference electrode of e.g. 80 cm$^2$ is placed in a contralateral fashion. The parameters for current (1 mA) and stimulation duration (10 min) in the case of prescribed limit values of current density are generated and limited by the control module and are stored by the monitoring and safety module. The particular advantages of tRNS applied on the move are its greater independence of the specific structure of the target area (folding) compared to the cathodal/anodal stimulation and the greater efficiency in the case of excitatory effects in the target areas (multiple opening of the Na+ channels). Finally, the safety aspects to be monitored are less dangerous because non-polarizing electrical currents appear to be safer in principle. However, one limitation compared to tDCS is that tRNS can at present only be used efficiently for stimulation, and less for inhibiting the activity of the target area.

Figure 5:
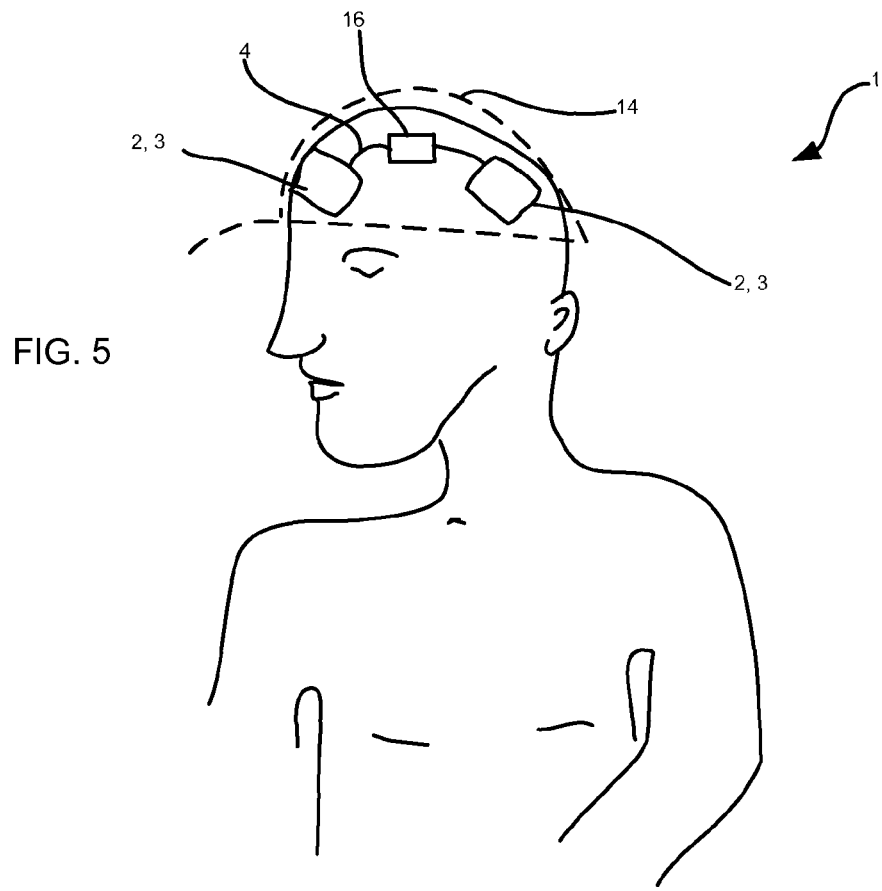
FIG. 5 shows an arrangement of the electrostimulation unit together with the electrodes in a hat in the helmet.

FIG. 5 shows a particularly advantageous embodiment of the invention, in which the stimulation generator 16, together with the electrodes 3, is integrated into a headgear embodied as a helmet 14, wherein the electrodes 3 are attached to a hat, which belongs to the helmet 14 and is pulled over the head.

The electrodes 3 are already positioned courtesy of being attached to the hat of the helmet 14, as a result of which it is easier for the user to handle the neurostimulation device 1. The stimulation generator 16 is operated by a remote control. By way of example, the latter is attached to the wrist of the user and connected to the control unit of the stimulation generator 16 in the helmet 14, either via a connection line 4 or wirelessly. A programmable cellular telephone, a PDA or a smartphone can be used as a remote control.

In an advantageous development (not illustrated in detail), the helmet 14 has a plurality of electrode partial areas 2, which are all connected to the stimulation generator 16 and can be individually actuated. The helmet 14, which is pulled onto the head of the user with the electrode partial areas 2 installed therein, is particularly suitable for safe operation of the stimulation device 1 because positioning of the electrodes 3 on the scalp is dispensed with. In the preferred embodiment, 500 electrode partial areas 2 are housed in the helmet 14 in a grid of 25 electrode partial areas 2 in the longitudinal direction and 20 electrode partial areas 2 in the transverse direction, with each electrode partial area being square with an appropriate size with a side length of between 8 and 18 millimeters. As a result, it is possible to position the electrodes 3 entirely independently of the user by, depending on the selected program, automatically actuating a plurality of electrode partial areas 2 in the region to be stimulated by means of the stimulation generator 16.

Advantageously, it is not only the position of the stimulation that is fixed by the number and position of the actuated electrodes 3 as a total electrode area, which is formed by electrode partial areas 2. According to a preferred development, the number of the electrode partial areas 2 actuated at one position is moreover used to react to boundary conditions, such as the electrode resistance (impedance) of the user. If there is high electrode resistance, more electrode partial areas 2 are actuated by the stimulation generator 16 for applying the required impulse strength than in the case of a low electrode resistance. At least individual electrode partial areas 2 are designed and connected as sensors for measuring the electrode resistance, and the established measured value is processed in the control unit.

The control algorithm for taking into account the electrode resistance interacts with the safety system, which is described in more detail. Thus, as a result of this arrangement it is possible, in each case and in a flexible fashion, to achieve the intended influencing of the membrane potentials in the target area that is suitable for the application. By way of example, the prefrontal cortex may be stimulated for smoker therapy, but, if need be, it is additionally possible to stimulate the insula. A further example clarifies the advantages of this embodiment. If, for example, a more focal stimulation of the target area is intended to be achieved, a higher current density can be achieved by means of a smaller switched electrode area, but this must be compensated for by the remaining parameters of the overall amount of charge induced.

Figure 6:
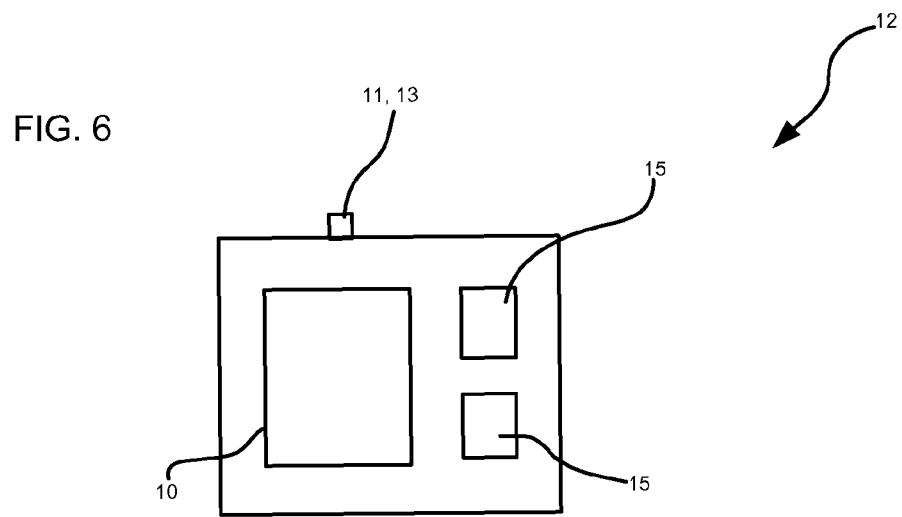
FIG. 6 shows an operating unit as a remote control.

FIG. 6 shows the remote control 12 with the function call buttons 15 and a display 10. The remote control 12 is connected to the stimulation generator 16 by means of connection lines (not illustrated) at the connectors 11.

However, the remote control 12 is preferably designed for wireless operation of the stimulation generator 16 and then has a transmission unit and a reception unit with an antenna 13, and also a current source.

Figure 7:
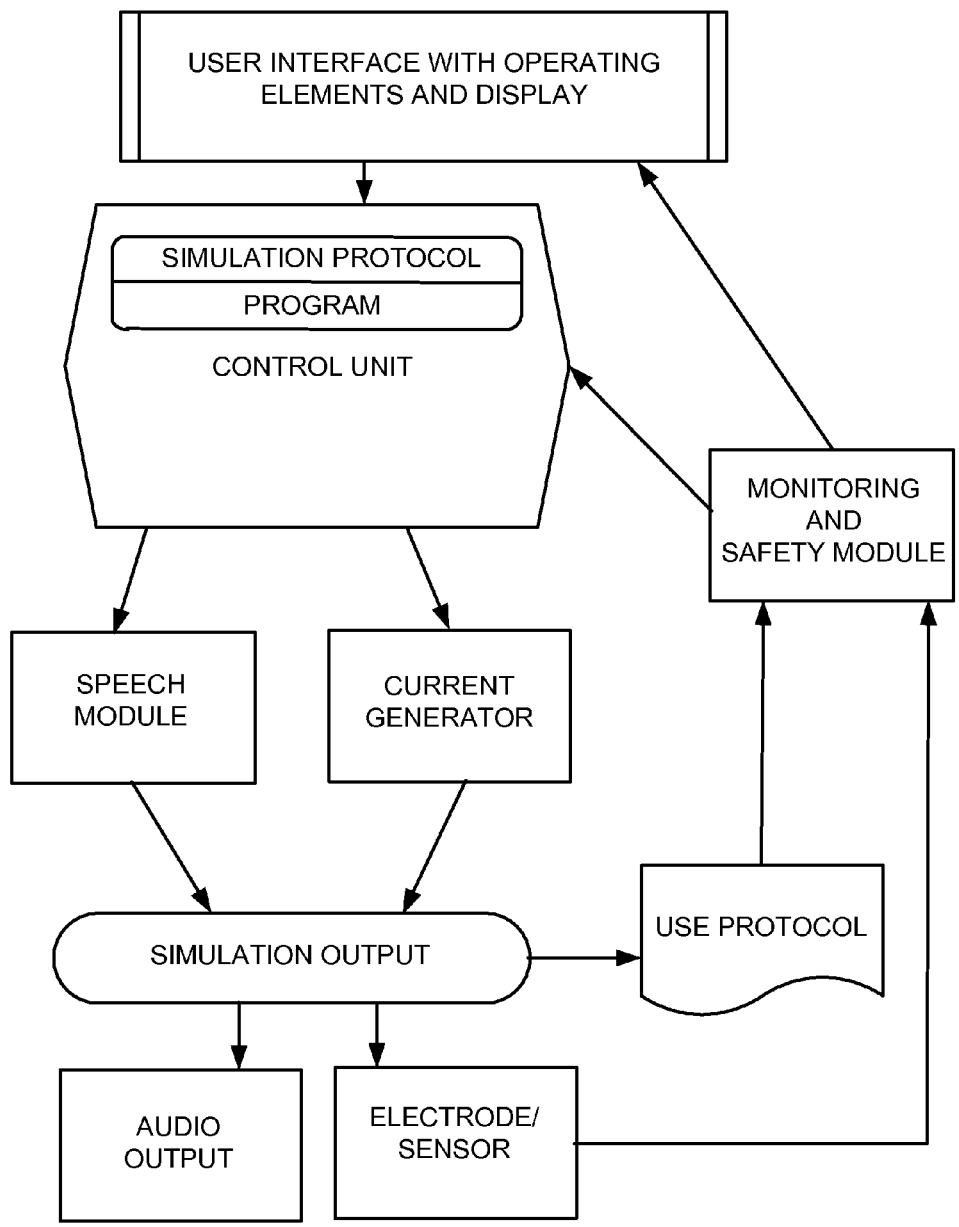
FIG. 7 shows a functional schematic of the electrostimulation unit.

FIG. 7 shows an overview of the control and regulating algorithm of the stimulation generator.

The user interface is used to select the program and the stimulation protocol, and these are converted into signals for the stimulation output via the control unit and the current generator and, if applicable, the speech module. The parameters are recorded in the use protocol and are transmitted to the monitoring and safety module for processing with the signals from the sensors. After evaluating and checking the data, it is output via a display in the user interface and there is feedback to the control unit of the stimulation generator.

The operating concept for the device consists of saving one or more stimulation programs with the corresponding electrical, topographic and temporal parameters in the control unit such that said stimulation programs can be called.

The utilized standard types of pulses are defined by the parameters current and voltage. Further parameters are the stimulation duration, the electrode area, the electrode position for the envisaged influencing of the activity of the target area, the amount of charge and the current density.

Suitable pulses with the respective characteristic, provided in the stimulation protocol for the intended use, are currents between 0.001 ampere and 0.002 ampere, occasionally also up to 0.005 ampere, and a stimulation duration of at most 900 seconds.

For reasons of safety, the stimulation control and the monitoring and safety module are functionally separated from the user interface and the remote control.

The control unit in turn directly interacts with the monitoring and safety module. The stimulation algorithm run-through is continuously monitored in respect of safety risks. These exist as an overdose of the stimulation in terms of magnitude or duration, caused by a program or hardware malfunction. There moreover is a risk from the occurrence of harmful surges. The correct seat of the electrodes is checked by monitoring the contact resistance. Thus, the action of the safeguarding system is able to interrupt the stimulation before one or more limit values, such as the maximum current, maximum stimulation time, overall amount of charge, and maximum current density, are exceeded. Additionally, the functions of charging the rechargeable battery are checked, and the latter is safeguarded against destruction by overcharging.

The use protocol stores the progress of the stimulation. Using this, it is possible to call information in respect of the last stimulation. However, this is also required to monitor time-integral variables. This particularly holds true for limiting the amount of charge used for the stimulation. The reports from the use protocol are routed to the user interface and may be read off from the display.

A current regulator is still switched upstream of the stimulation output and likewise connected to the use protocol.

The stimulation is controlled according to the program selected by the user. The control is monitored by a monitoring and safety module, which carries out the following functions:

The unit monitors and limits the current and the introduced power. This excludes the possibility of injury and ensures that the current lies below the stimulus threshold.

The contact resistance of the electrodes is monitored to exclude the possibility of injury as the contact resistance increases. Increasing contact resistance can also be traced back to a partly or entirely detached electrode. In this case, the current density during the stimulation must be limited by additionally switching further suitable electrode areas or the stimulation is interrupted.

A too intensive stimulation is feasible as a result of an erroneous operation or a defect. The possibility of this going hand-in-hand with an excessively high electrolytic load on the tissue must be excluded, as must the possibility of damage to the tissue as a result of ion transport. It is for this reason that the unit monitors and limits the amount of charge transferred per hour and the overall amount of charge.

A pulsed stimulation could occur if a cable breaks or an electrode becomes detached. A pulsed current has a significantly lower stimulus threshold and may already be painful at low currents. It is for this reason that the unit identifies a loose connection by using the control unit, and interrupts the stimulation in this case.

The microcontroller is equipped with a simple, yet efficient, extremely energy-saving monitoring apparatus, which has operational-current-independent battery back-up in the case of a malfunction, in order to counter errors during the program progress or deviations in the stimulation procedure from the control algorithm and to counter a crash of the control software. The microcontroller in the monitoring and safety module is equipped with a watchdog system, which requires a precisely fixed signal sequence from the program, in each case after a unit of time, for example every 10 ms. If the signal sequence fails, the monitoring apparatus generates a reset of the control and, if necessary, forces a restart of the software.

If the control program reaches an undefined state as the result of a defect, a programming error, or high-energy radiation, it is interrupted after 10 ms in a worst-case scenario and, if necessary, it is restarted. Hence, the possibility of being in danger is excluded, even in the case of complicated control software and hard usage conditions.

The safety-relevant control functions operate according to the journaling principle, an automatic use protocol is maintained such that all stimulation procedures are traceable. By way of example, if the stimulation program provides for an increase in the stimulus current, the program generates an entry in the journal, which entry contains the current algorithm program step and the increase of the current. At the end, it appends the undertaken change into the journal. A restart of the control software thus continues all safety-relevant functions without transition and without loss of information. The current regulator is switched upstream of the stimulation output.

The remote control is secured by cryptographic means and the transmitter unit is physically separated from the other control units. This ensures that no other remote control can trigger a stimulation.

The following are further technical parameters of the stimulation generator:

A mobile transcranial stimulation generator, powered by rechargeable batteries and controlled by a microcontroller Dimensions: 80×60×25 mm.

In the preferred embodiment, the amount of charge is limited to 600 mAs within 2 hours.

In the case of a defect or mechanical destruction, the current is limited by hardware and microcontroller with a separate, operational-current-independent battery backed-up energy supply.

The contact resistance is monitored in order to avoid injury and identify detached electrodes.

The charge state of the rechargeable battery is displayed, optionally with a warning signal.

The period of use with one battery charge is longer than 24 hours.

Use protocols are maintained even if the current supply fails.

A remote control provides the user with unimpeded, always available auto-stimulation, even in the most diverse types of natural everyday situations. As a result, the user's freedom of movement is optimally matched to the requirements of the various fields of application.

List of Reference Signs

1 Neurostimulation device
2 Electrode partial areas, arranged in a grid-like fashion,
3 Large-area electrodes
4 Electrical connection lines
5 Cathode
6 Anode
7 Inion
8 Attachment band
9 Program selection buttons, power button, call button for use protocol
10 Display of the user interface or the remote control
11 Connectors
12 Operating unit as a remote control
13 Transmitter/receiver with antenna
14 Helmet
15 Function call buttons
16 Stimulation generator

The invention claimed is:

1. A mobile device for transcranial auto-stimulation, comprising:
   electrodes with attachment means for precise positioning on the scalp and electrical connection lines; and
   a transportable, miniaturized stimulation generator with:
      a current generator, and
      a control unit, in which it is possible to store at least one program for determining the pulses to be emitted by the current generator in respect of the value range of the electrical, topographic and temporal parameters, and which is designed such that the overall charge amount and the current density can be detected and the duration and strength of the stimulation can be controlled in view of the size admissible in each case and provided for calling;
   a user interface with:
      a program selection button for selecting the programs stored in the control unit,
      at least one function call button for selecting and calling provided stimulation protocols,
   a display;
   an electric energy reservoir;
   a monitoring and safety module for checking and limiting the current, the stimulation duration, the electrode position and the electrode area, wherein the monitoring and safety module has a separate electric energy reservoir.

2. The device according to claim 1, wherein the function call buttons for calling a stimulation protocol from a program by the user, or the entire user interface, are designed as a remote control for the stimulation generator.

3. The device according to claim 1, wherein the monitoring and safety module has a separate microcontroller and a capacitor as a separate energy reservoir for a battery backed-up current supply in the case of a malfunction.

4. The device according to claim 1, wherein the electrodes are formed from electrode partial areas with an area of less than 25 $cm^2$ and in that a multiplicity of electrode partial areas are arranged in a grid-like fashion, wherein the electrodes can be formed by actuating one or more electrode partial areas.

5. The device according to claim 1, wherein the attachment means for the electrodes are designed as a headgear and the electrodes are integrated into the headgear.

6. The device according to claim 5, wherein the stimulation generator is integrated into the headgear.

7. The device according to claim 1, wherein a speech module is provided in the stimulation generator or separate therefrom, by means of which speech module spoken commands, coupled via the stimulation protocol, can be output via headphones.

8. The device according to claim 2, wherein the stimulation generator has an attachment band for attaching it to the upper arm, the hand or to the chest of the user, and in that the remote control with the function call buttons is designed for wireless action on the control unit of the stimulation generator.

9. The device according to claim 1, wherein the electrodes or the electrode partial areas are designed as sensors for establishing the contact resistance.

10. The device according to claim 1, wherein the user interface contains a display for visual monitoring of functional states of the instrument and the current operator control actions.

11. A method for controlling and regulating a mobile device for transcranial auto-stimulation according to claim 1, the method comprising the following steps:
selecting a program based on a selection made using the program selection button on the user interface;
selecting a stimulation protocol based on a selection made with the function call buttons;
monitoring and limiting stimulation by means of the monitoring and safety module of the stimulation generator; and
matching the parameters current, voltage, stimulation duration, electrode position and electrode area to one another such that predefined limiting values are not exceeded.

12. The method according to claim 11, wherein the presence of a precisely set signal sequence is checked by the control unit and monitored in a quasi-continuous fashion, and, if errors are detected, a termination or restart of the program is enforced.

13. The method according to claim 11, wherein the contact resistance is measured by the electrodes designed as sensors and the measured value is reported to the control unit and processed, and, for the purposes of stimulation, a corresponding number of the multiplicity of electrode partial areas, positioned in a grid-like fashion, are actuated such that the required strength of the stimulation current is obtained over a minimum total electrode area in the interests of precise focusing.

14. The method according to claim 11, wherein the course of the stimulation and the information on the last stimulation for monitoring and limiting time-integral variables can be stored and called.

* * * * *